United States Patent [19]
Vandenberk et al.

[11] Patent Number: 5,919,788
[45] Date of Patent: Jul. 6, 1999

[54] 4-(1H-INDOL-1-YL)-1-PIPERIDINYL DERIVATIVES

[75] Inventors: Jan Vandenberk, Beerse; Ludo Edmond Josephine Kennis, Turnhout; Josephus Carolus Mertens, Oud-Turnhout, all of Belgium

[73] Assignee: Janssen Pharmaceutica, N.V., Beerse, Belgium

[21] Appl. No.: 08/860,380

[22] PCT Filed: Jan. 23, 1996

[86] PCT No.: PCT/EP96/00363

§ 371 Date: Jun. 27, 1997

§ 102(e) Date: Jun. 27, 1997

[87] PCT Pub. No.: WO96/23784

PCT Pub. Date: Aug. 8, 1996

[30] Foreign Application Priority Data

Jan. 31, 1995 [EP] European Pat. Off. .............. 95200229

[51] Int. Cl.⁶ ...................... A61K 31/505; C07D 471/04; C07D 487/04
[52] U.S. Cl. .......................... 514/258; 514/269; 514/278; 514/322; 544/278; 544/281; 544/282; 544/315; 546/18; 546/199
[58] Field of Search ..................... 514/258, 269, 514/278, 322; 544/278, 281, 282, 315; 546/18, 199

[56] References Cited

U.S. PATENT DOCUMENTS

| | | |
|---|---|---|
| 4,342,870 | 8/1982 | Kennis et al. ............... 544/282 |
| 4,443,451 | 4/1984 | Kennis et al. ............... 424/251 |
| 5,140,029 | 8/1992 | Kennis et al. ............... 514/272 |
| 5,284,854 | 2/1994 | Kennis et al. ............... 514/272 |
| 5,360,807 | 11/1994 | Janssens et al. ............. 514/318 |
| 5,532,372 | 7/1996 | Saji et al. ................... 544/368 |
| 5,665,732 | 9/1997 | Baker et al. ................. 514/307 |

FOREIGN PATENT DOCUMENTS 0 470 039 A2  2/1992  European Pat. Off. ...... C07D 209/08

OTHER PUBLICATIONS

Andersen et al., "Selective Centrally Acting Serotonin 5–$HT_2$ Antagonists. 2. Substituted 3–(4–Fluorophenyl)–1H–Indoles", J. Med. Chem., 1992, 35, 4823–4831.

*Primary Examiner*—Ceila Chang
*Attorney, Agent, or Firm*—Mary Appollina

[57] ABSTRACT

The present invention concerns the compounds of formula

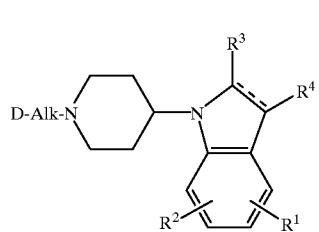

(I)

the pharmaceutically acceptable addition salts and the stereochemically isomeric forms thereof, wherein the dashed line designates an optional bond; $R^1$ and $R^2$ are each independently hydrogen, halogen, $C_{1-6}$alkyl or $C_{1-6}$alkyloxy; $R^3$ and $R^4$ are each independently hydrogen, $C_{1-6}$alkyl, phenyl or phenyl substituted with one, two or three substituents selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)-amino, carboxyl, $C_{1-6}$alkyloxycarbonyl and $C_{1-6}$alkylcarbonyl; Alk is $C_{1-4}$alkanediyl; D is a pyrimidinone, piperidone or a benzimidozolidinone; having antipsychotic activity; their preparation, compositions containing them and their use as a medicine.

15 Claims, No Drawings

4-(1H-INDOL-1-YL)-1-PIPERIDINYL DERIVATIVES

CROSS-REFERENCE TO RELATED APPLICATIONS

This application is a 371, the national stage of application No. PCT/EP 96/00363, filed on Jan. 23, 1996, which application claims priority from EP 95.200.229.3, filed on Jan. 31, 1995.

The present invention concerns 4-(1H-indol-1-yl)-1-piperidinyl derivatives having therapeutic potential in psychotic disorders. It further relates to their preparation, compositions comprising them and their use as a medicine.

In EP-A-0,037,265, published on Oct. 7, 1981, EP-A-0,070,053, published on Jan. 19, 1983, and in EP-A-0,378,255, published on Jul. 18, 1990, there are described a number of 5-[[4-(1H-indol-3-yl)-1-piperidinyl]alkyl]-4(3H)-pyrimidinone derivatives having antipsychotic, antihistaminic and antiserotonergic activity. Structurally, the compounds of the present invention differ therefrom in that the 4 position of their piperidine moiety is invariably substituted by a 1H-indol-1-yl derivative.

EP-A-0,470,039, published on Feb. 5, 1992, discloses 4-(3-aryl-1H-indol-1-yl)-1-piperidinyl derivatives as selective antagonists of the serotonin 5-HT$_2$ receptor without substantial dopamine D-2 antagonistic activity both in vivo and in vitro. Said selective antagonistic property is measured as the ratio between the dopamine D-2 receptor and the serotonin 5-HT$_2$ receptor antagonistic activities. Unexpectedly, the compounds of the present invention differ therefrom in that they exhibit central dopamine and central serotonin antagonistic activity in vivo in similar dose-ranges, i.e. the ratio between central doparninergic and central serotonergic activity is about unity.

The compounds of the present invention show antipsychotic activity with an unexpected increased cardiovascular safety, i.e. they show an improved dissociation between the peripheral α-adrenergic antagonistic activity and the central dopamine and serotonin antagonistic activity.

The present invention concerns the compounds of formula

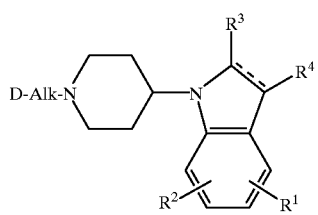

(I)

the pharmaceutically acceptable addition salts and the stereochemically isomeric forms thereof, wherein:
  the dashed line designates an optional bond;
  $R^1$ and $R^2$ are each independently hydrogen, halogen, $C_{1-6}$alkyl or $C_{1-6}$alkyloxy;
  $R^3$ and $R^4$ are each independently hydrogen, $C_{1-6}$alkyl, phenyl or phenyl substituted with one, two or three substituents selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl;
  Alk is Cl 4alkanediyl;

D is a radical of formula

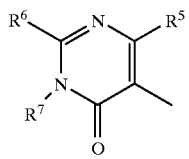

(a)

wherein
  $R^5$ is hydrogen or $C_{1-6}$alkyl;
  $R^6$ is hydrogen, $C_{1-6}$alkyl, $C_{1-6}$alkyloxy, $C_{1-6}$alkylthio, amino or mono- or di($C_{1-6}$alkyl)amino; and
  $R^7$ is hydrogen or $C_{1-6}$alkyl; or
  $R^6$ and $R^7$ taken together may form a bivalent radical —$R^6$—$R^7$—, in particular, —$R^6$—$R^7$— may be

| | |
|---|---|
| —CH$_2$—CH$_2$—CH$_2$— | (a-1); |
| —CH$_2$—CH$_2$—CH$_2$—CH$_2$— | (a-2); |
| —CH=CH—CH$_2$— | (a-3); |
| —CH$_2$—CH=CH— | (a-4) or |
| —CH=CH—CH=CH— | (a-5); | wherein one or two hydrogen atoms of said radicals (a-1) to (a-5) each independently may be replaced by $C_{1-6}$alkyl, hydroxy, $C_{1-6}$alkyloxy or $C_{1-10}$alkylcarbonyloxy; or —$R^6$—$R^7$— may also be

| | |
|---|---|
| —S—CH$_2$—CH$_2$— | (a-6); |
| —S—CH$_2$—CH$_2$—CH$_2$— | (a-7); |
| —S—CH=CH— | (a-8); |
| —NH—CH$_2$—CH$_2$— | (a-9); |
| —NH—CH$_2$—CH$_2$—CH$_2$— | (a-10); |
| —NH—CH=CH— | (a-11); |
| —NH—CH=N— | (a-12); |
| —S—CH=N— | (a-13) or |
| —CH=CH—O— | (a-14); | wherein one or where possible two or three hydrogen atoms in said radicals (a-6) to (a-14) each independently may be replaced by $C_{1-6}$alkyl; or D is a radical of formula

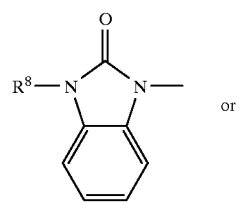

(b)

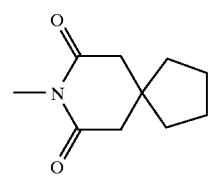

(c)

wherein $R^8$ is hydrogen or $C_{1-6}$alkyl.

As used in the foregoing definitions the term halogen is generic to fluoro, chloro, bromo and iodo. The term $C_{1-4}$alkyl defines straight and branched saturated hydrocarbons, having from 1 to 4 carbon atoms such as, for example, methyl, ethyl, propyl, butyl, 1-methylethyl, 1,1- dimethylethyl, 2-methylpropyl. The term $C_{1-6}$alkyl is meant to include $C_{1-4}$alkyl radicals and the higher homologues thereof having 5 or 6 carbon atoms such as, for example, pentyl, hexyl and the like. The term $C_{1-10}$alkyl is meant to include $C_{1-6}$alkyl radicals and the higher homologues thereof having 7 to 10 carbon atoms such as, for example, heptyl, octyl, nonyl, decyl and the like. The term $C_{2-4}$alkanediyl defines bivalent straight or branch chained alkanediyl radicals having from 2 to 4 carbon atoms such as, for example, 1,2-ethanediyl, 1,3-propanediyl, 1,4-butanediyl and the like. The term $C_{1-4}$alkanediyl is meant to include $C_{2-4}$alkanediyl radicals and the lower homologue, i.e. 1,1-methanediyl.

The addition salts as mentioned herein are meant to comprise the therapeutically active addition salt forms which the compounds of formula (I) are able to form with appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are also meant to comprise the therapeutically active non-toxic base, in particular, a metal or amine addition salt forms which the compounds of formula (I) are able to form. Said salts can conveniently be obtained by treating the compounds of formula (I) containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted by treatment with an appropriate base or acid into the free acid or base form.

The term addition salt as used hereinabove also comprises the solvates which the compounds of formula (I) are able to form and said solvates are meant to be included within the scope of the present invention. Examples of such solvates are, e.g. the hydrates, alcoholates and the like.

The term stereochemically isomeric forms as used herein defines all the possible isomeric forms in which the compounds of formula (I) may occur. Unless otherwise mentioned or indicated, the chemical designation of compounds denotes the mixture of all possible stereochemically isomeric forms, said mixtures containing all diastereomers and enantiomers of the basic molecular structure.

Some of the compounds of formula (I) may also exist in their tautomeric forms. Such forms although not explicitly indicated in the above formula are intended to be included within the scope of the present invention.

Whenever used hereinafter, the term compounds of formula (I) is meant to include also the pharmaceutically acceptable addition salts and all stereoisomeric forms.

Interesting compounds are those compounds of formula (I) wherein D is a radical of formula

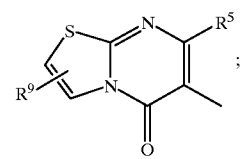
(d-1)

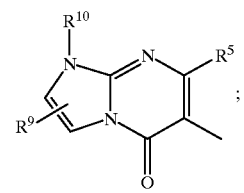
(d-2)

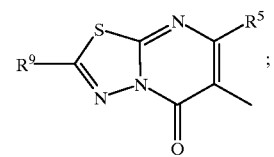
(d-3)

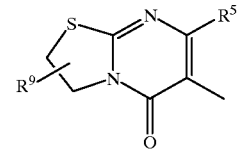
(d-4)

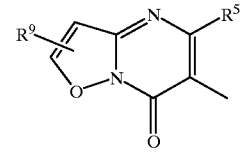
(d-5)

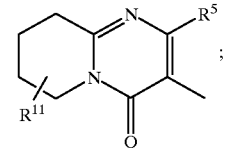
(d-6)

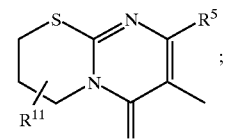
(d-7)

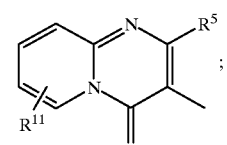
(d-8)

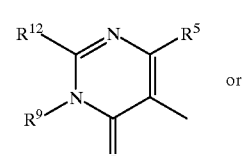
or
(d-9)

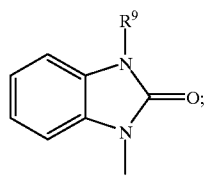

(d-10)

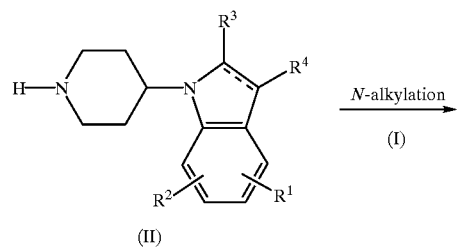

(II)

wherein $R^5$ is hydrogen or $C_{1-6}$alkyl and preferably is methyl; $R^9$ and $R^{10}$ each independently are hydrogen or $C_{1-6}$alkyl; $R^{11}$ is $C_{1-6}$alkyl, hydroxy, $C_{1-6}$alkyloxy or $C_{1-10}$alkylcarbonyloxy, and preferably is hydroxy, $C_{1-6}$alkyloxy or $C_{1-10}$alkyl-carbonyloxy; and $R^{12}$ is hydrogen, $C_{1-6}$alkyl, $C_{1-6}$alkyloxy, $C_{1-6}$alkylthio, amino or mono- or di($C_{1-6}$alkyl)amino.

Further interesting compounds are those compounds of formula (I) wherein $R^3$ and $R^4$ are both hydrogen.

In a first subset of compounds of formula (1), Alk is $C_{2-4}$alkanediyl.

In a second subset of compounds of formula (I), $R^1$ is hydrogen or halogen and $R^2$ is hydrogen.

In a third subset of compounds of formula (I), the substituent on the 4 position of the piperidinyl is an 1H-indole, i.e. the dashed line represents an extra bond.

In a fourth subset of compounds of formula (I), the substituent on the 4 position of the piperidinyl is an 2,3-dihydro-1H-indole.

Preferred compounds are those compounds of formula (I) wherein $R^1$ is hydrogen or fluor; $R^2$, $R^3$ and $R^4$ are hydrogen; Alk is 1,2-ethanediyl; D is a radical of formula (a) wherein $R^5$ is methyl; $R^6$ is $C_{1-6}$alkylamino and $R^7$ is $C_{1-6}$alkyl; or $R^6$ and $R^7$ taken together may form a bivalent radical of formula (a-2) or (a-5) wherein one hydrogen atom of said radicals (a-2) and (a-5) may be replaced by $C_{1-6}$alkyl, hydroxy or $C_{1-6}$alkyloxy; or $R^6$ and $R^7$ taken together may form a bivalent radical of formula (a-6), (a-7), (a-8), (a-13) or (a-14) wherein one or where possible two hydrogen atoms may be replaced by $C_{1-6}$alkyl.

More preferred compounds are those preferred compounds wherein the substituent on the 4 position of the piperidinyl is an indole wherein $R^1$ is substituted in the 5 position and stands for hydrogen or fluor.

Most preferred compounds are selected from
3-[2-[4-(5-fluoro-1H-indol-1-yl)-1-piperidinyl]ethyl]-6,7,8,9-tetrahydro-2-methyl-4H-pyrido[1,2-a]pyrimidin-4-one;
6-[2-[4-(5-fluoro-1H-indol-1-yl)-1-piperidinyl]ethyl]-7-methyl-5H-thiazolo[3,2-a]-pyrimidin-5-one;
5-[2-[4-(5-fluoro-1H-indol-1-yl)-1-piperidinyl]ethyl]-3,6-dimethyl-2-(methylamino)-4(3H)-pyrimidinone; and
2,3-dihydro-6[2-[4-(1H-indol-1-yl)-1-piperidinyl]ethyl]-7-methyl-5H-thiazolo[3,2-a]-pyrimidin-5-one;
the pharmaceutically acceptable addition salts and the stereochemically isomeric forms thereof.

The compounds of formula (I) can generally be prepared by N-alkylating a 1-(piperidin-4-yl)-1H-indole derivative of formula (II) with an alkylating reagent of formula (III) following the procedure described in EP-A-0,037,265, EP-A-0,070,053, EP-A-0,196,132 and in EP-A-0,378,255.

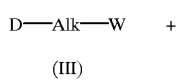

(III)

In the following intermediates, the dashed line and the radicals D, Alk and $R^1$ to $R^4$ are defined as under formula (1) unless otherwise specified. In intermediate (III), W represents an appropriate reactive leaving group such as, for example, halo, e.g. chloro, bromo or iodo; sulfonyloxy, e.g. methanesulfonyloxy, 4-methylbenzenesulfonyloxy.

In this and the following preparations, the reaction products may be isolated from the reaction medium and, if necessary, further purified according to methodologies generally known in the art such as, for example, extraction, crystallization, trituration and chromatography.

Compounds of formula (1) wherein $R^3$ and $R^4$ are hydrogen and the heterocyclic moiety in the 4 position of the piperidine ring is an 1H-indole, said compounds being represented by formula (I-f), may alternatively be prepared by cyclizing an intermediate of formula (IV) wherein W is a reactive leaving group such as, for example, halo, e.g. chloro, bromo or iodo; sulfonyloxy, e.g. methanesulfonyloxy, 4 -methylbenzene-sulfonyloxy, in the presence of a reductant such as, for example, a complex metal hydride, e.g. sodium borohydride. Said procedure is described in Synthetic Communications, 18(3), 265–273 (1988).

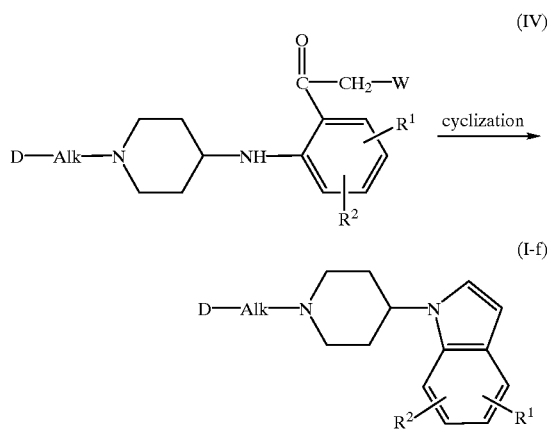

EP-A-0,037,265, EP-A-0,070,053, EP-A-0,196,132 and EP-A-0,378,255 describe other alternative procedures to prepare compounds of formula (I). Furthermore, the compounds of formula (I) may be converted into each other following art-known functional group transformation reactions.

A number of intermediates and starting materials are known compounds which may be prepared according to art-known methodologies. For example, intermediates of formula (III) and their preparations are described in EP-A-0,037,265, EP-A-0,070,053, EP-A-0,196,132 and in EP-A-0,378,255.

Intermediates of formula (II) can be prepared following art-known procedures, e.g. by reductively aminating a ketone of formula (V), wherein P is a protecting group such as, for example, an alkyloxycarbonyl group, with an indole derivative of formula (VI), and subsequently removing the protecting group P by art-known deprotection techniques.

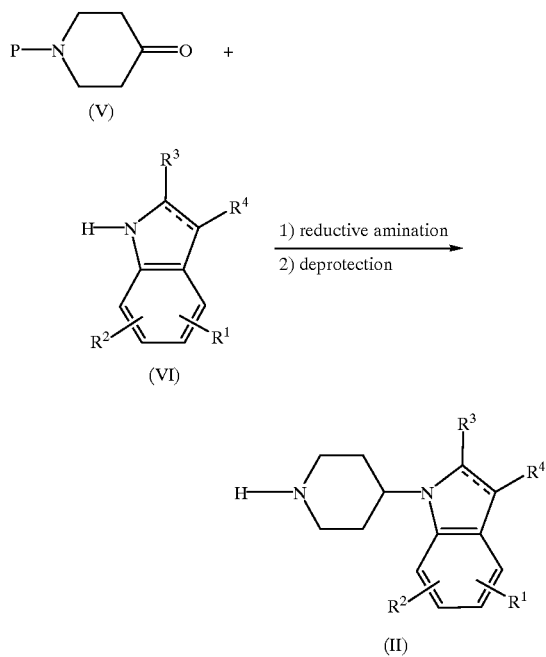

Said reductive amination may conveniently be carried out by mixing the reactants in a suitable reaction-inert solvent such as, for example, methanol or toluene, with an appropriate reductant. Preferably, the ketone of formula (V) is first reacted with the indole derivative of formula (VI) to form an enamine, which is subsequently reduced. Hydrogen in the presence of a suitable catalyst such as, for example, palladium or platinum supported on for instance charcoal may be used as an appropriate reductant. Elevated pressure and/or temperature may enhance the rate of the reaction. In order to prevent the undesired further hydrogenation of certain functional groups in the reactants and the reaction products, it may be advantageous to add an appropriate catalyst poison to the reaction mixture such as, for example, thiophene.

The intermediates of formula (VI) wherein the dashed line represents an extra bond and $R^3$ and $R^4$ are both hydrogen, may be prepared as described in Journal of Heterocyclic Chemistry, 2, 298–299 (1965).

Some of the compounds of formula (I) and some of the intermediates in the present invention contain at least one asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers.

Pure stereochemically isomeric forms of the compounds of formula (I) may also be obtained from the pure stereochemically isomeric forms of the appropriate intermediates and starting materials, provided that the intervening reactions occur stereospecifically. The pure and mixed stereochemically isomeric forms of the compounds of formula (I) are intended to be embraced within the scope of the present invention.

The compounds of formula (I), the pharmaceutically acceptable addition salts and stereochemically isomeric forms thereof, are antagonists of neurotransmitters and in particular of the mediators serotonin and dopamine. Antagonizing said mediators will suppress or relieve a variety of symptoms associated with phenomena induced by the release, in particular the excessive release, of these mediators. Therapeutic indications for using the present compounds are mainly in the CNS area, especially in psychotic disorders. Further, serotonin is a potent broncho- and vasoconstrictor and thus the present antagonists may be used against hypertension and vascular disorders. In addition, serotonin antagonists have been associated with a number of other properties such as, the suppression of appetite and promotion of weight loss, which may prove effective in combatting obesity; and also the alleviation of withdrawal symptoms in addicts trying to discontinue drinking and smoking habits. The present compounds also appear to be useful therapeutic agents for combatting autism.

In view of the usefulness of the subject compounds in the treatment of diseases associated with the release of neurotransmitters, in particular in the treatment of psychotic diseases, the present invention provides a method of treating warm-blooded animals suffering from such diseases, in particular psychotic diseases, said method comprising the systemic administration of an antipsychotic amount of a compound of formula (I) or a pharmaceutically acceptable addition salt thereof, effective in treating diseases associated with the release of neurotransmitters, in particular psychotic diseases. Those of skill in the treatment of such diseases could readily determine the effective amount from the test results presented hereinafter. In general it is contemplated that an effective antipsychotic daily amount would be from about 0.01 mg/kg to about 4 mg/kg body weight, more preferably from about 0.04 mg/kg to about 2 mg/kg body weight.

The present invention thus also relates to compounds of formula (I) as defined hereinabove for use as a medicine. Further, the present invention also relates to the use of a compound of formula (I) for the manufacture of a medicament for treating psychotic diseases.

The "apomorphine, tryptamine, norepinephrine (ATN) test in rats" is used to evaluate dopamine antagonism, serotonin antagonism and α-adrenergic antagonistic properties of the compounds of formula (I). In said test, which is described hereinafter, rats are observed for effects which are indicative for peripheral and central activity of the tested compounds. Centrally acting serotonin antagonists are potential antipsychotic drugs, in particular when simultaneously displaying dopamine antagonism. Peripheral serotonin antagonists are potentially useful in the gastro-intestinal and cardiovascular field, in particular when simultaneously displaying α-adrenergic antagonistic activity. The compounds of the present invention show a strong central dopamine and serotonin antagonism and little peripheral α-adrenergic antagonistic activity. In view of the central dopamine and serotonin antagonistic activity of the compounds of formula (I), they are particularly useful in combatting psychoses, aggressive behaviour, anxiety, depression and migraine. Furthermore, the improved dissociation between peripheral α-adrenergic antagonistic activity and central dopamine and serotonin antagonistic activity of the compounds of formula (I) over prior known antipsychotic agents, leads to an increased cardiovascular safety, i.e. a decreased likelihood of hypotension.

For administration purposes, the subject compounds may be formulated into various pharmaceutical forms. To prepare the pharmaceutical compositions of this invention, an effective amount of the particular compound, in addition salt or in free acid or base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Addition salts of (I) due to their increased water solubility over the corresponding free base or free acid form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate and not to limit the scope of the present invention.

EXPERIMENTAL PART

Hereinafter, "RT" means room temperature and "DIPE" means diisopropyl ether.

A. Preparation of the intermediates

EXAMPLE 1 a) Sodium methylate (1260.5 g) was added dropwise to a suspension of thiourea (373 g) in ethanol (1750 ml) and the dropping funnel was rinsed with ethanol (175 ml). The mixture was heated to 40° C. and 3-acetyldihydro-2(3H)-furanone (448.5 g) was added dropwise. The dropping funnel was rinsed with ethanol (475 ml) and the reaction mixture was stirred and refluxed for 6.25 hours. Stirring was continued for 2 hours, while cooling. The solvent was evaporated and the residue was dissolved in water (2800 ml). This mixture was cooled on ice and neutralized with hydrochloric acid (490 ml) The precipitate was filtered off, washed with water (350 ml) and dried, yielding 268 g (41.1%) of 5-(2-hydroxyethyl)-2-mercapto-6-methyl-4 (3H)-pyrimidinone (intermediate 1).

b) A mixture of intermediate 1 (37.2 g) and sodium methylate (36 g) in methanol (250 ml) was stirred for 30 min. Ethane iodide (31.2 g) was added dropwise. The reaction mixture was stirred and refluxed for 3 hours. The solvent was evaporated and the residue was stirred in water, filtered and recrystallized from $CH_3CN$. The precipitate was filtered off and dried, yielding 26 g (60%) of 2-(ethylthio)-5-(2-hydroxyethyl)-6-methyl-4(3H)-pyrimidinone (intermediate 2).

c) Potassium hydroxide (8.4 g) was added to a solution of intermediate 2 (33 g) in dimethyl sulfoxide (150 ml). The mixture was stirred for 1 hour at 60–70 ° C. The mixture was cooled to 20° C. and iodomethane (21.3 g) was added dropwise. The reaction mixture was stirred overnight at RT. The mixture was poured out into water and extracted with toluene. The separated organic layer was dried, filtered and the solvent was evaporated. The residue was crystallized from 4-methyl-2-pentanone and the precipitate was filtered off and dried, yielding 16 g (46%) of 2-(ethylthio)-5-(2-hydroxy-ethyl)-3,6-dimethyl-4(3H)-pyrimidinone (intermediate 3).

EXAMPLE 2 a) 3-acetyldihydro-2(3H)-furanone (25.6 g) was added to a stirred mixture of acetamidine hydrochloride (20 g) and sodium methylate (110 g) in methanol (150 ml). The reaction mixture was stirred and refluxed overnight. The reaction mixture was cooled and acetic acid (36 g) was added dropwise. The precipitate was filtered off and the filtrate evaporated. The residue was purified by column chromatography over silica gel (eluent: $CHCl_3/(CH_3OH/NH_3)$ 90/10). The pure fractions were collected and the solvent was evaporated. The residue was crystallized from 2-propanol. The crystals were filtered off and dried, yielding 7.6 g (22%) of 5-(2-hydroxyethyl)-2,6-dimethyl-4(3H)-pyrimidinone (intermediate 4).

b) Sodium methylate (1.9 g) was added to a mixture of intermediate 4 (6 g) in methanol (50 ml) while stirring at RT. Stirring was continued for 30 minutes and iodomethane (5 g) was added dropwise and the reaction mixture was stirred and refluxed for 4 hours. The solvent was evaporated, water was added to the residue and this mixture was extracted with $CH_2Cl_2$. The organic layer was separated, dried over $MgSO_4$, filtered and the solvent was evaporated, yielding 6.0 g (94%) of 5-(2-hydroxyethyl)-2,3,6-trimethyl-4(3H)-pyrimidinone (intermediate 5).

EXAMPLE 3 a) A mixture of ethyl 4-oxo-1-piperidinecarboxylate (85 g) and 2,3-dihydro-1H-indole (60 g), palladium on activated carbon (10%) (4 g) and a solution of thiophene in isopropyl ether (4%) (2 ml) in methanol (700 ml) was reacted in a Parr Pressure Vessel at 50° C. overnight. After completion, the mixture was filtered and the filtrate was evaporated, yielding 80 g (58%) of ethyl 4-(2,3-dihydro-1Hindol-1-yl)-1-piperidine-carboxylate (intermediate 6)

b) A mixture of intermediate 6 (95 g) and potassium hydroxide (194 g) in 2-propanol (1300 ml) was stirred and refluxed for 24 hours. The solvent was evaporated and the residue was dissolved in $H_2O/CH_2Cl_2$. The organic layer was separated, dried over $MgSO_4$, filtered and evaporated, yielding 64 g (90.4%) of 2,3-dihydro-1-(4-piperidinyl)-1H-indole. A sample (4.5 g) was crystallized from $CH_3OH$ and converted into the hydrochloric acid salt (1:1) in 2-propanol and filtered off, yielding 3.0 g of 2,3-dihydro-1-(4-piperidinyl)-1H-indole monohydrochloride (intermediate 7).

EXAMPLE 4

A mixture of 2-bromoethanol (3.75 g), 1-(4-piperidinyl)-1H-indole (5 g) and sodium hydrogen carbonate (4.2 g) in ethanol (100 ml) was stirred and refluxed overnight. The solvent was evaporated. The residue was stirred in water and this mixture was extracted with $CH_2Cl_2$. The separated organic layer was dried over $MgSO_4$, filtered and the solvent was evaporated. The residue was purified by column chromatography over silica gel (eluent: $CH_2Cl_2/CH_3OH$ 95/5). The pure fractions were collected and the solvent was evaporated. The residue was stirred in DIPE and the solvent was evaporated, yielding 4 g (64%) of 4-(1H-indol-1-yl)-1-piperidineethanol (intermediate 8).

EXAMPLE 5 a) A mixture of 2-amino-3-pyridinol (100 g), 3-acetyldihydro-2(3H)-furanone (100 g), 4-methylbenzene sulfonic acid (1 g) and xylene (700 ml) was stirred and refluxed overnight using a water separator. The mixture was cooled and the product was filtered off and dried. The product was converted into the hydrochloric acid salt in 2-propanol. The salt was filtered off and dried, yielding 120 g (58.4%) of 9-hydroxy-3-(2-hydroxy-ethyl)-2-methyl-4H-pyrido[1,2-a]pyrimidin-4-one monohydrochloride (intermediate 9).

b) Dimethyl sulfate (2.52 g) was added dropwise to a mixture of intermediate 9 (4.4 g) and sodium hydroxide (0.8 g) in water (10 ml), while cooling in ice water. The reaction mixture was stirred for 15 minutes at RT, then it was heated for 1 hour using a warm water bath. The reaction mixture was cooled and extracted with $CH_2Cl_2$. The precipitate in the separated aqueous layer was filtered off and purified by column chromatography over silica gel (eluent: $CH_2Cl_2/CH_3OH$ 97/3). The pure fractions were collected and the solvent was evaporated. The residue was crystallized from $CH_3CN$. The crystals were filtered off and dried, yielding 2 g (42%) of 3-(2-hydroxyethyl)-9-methoxy-2-methyl-4H-pyrido[1,2-a]pyrimidin-4-one (intermediate 10).

c) A mixture of intermediate 10 (14 g) in methanol (250 ml) was hydrogenated at 50° C. with palladium on activated carbon (10%) (2 g) as a catalyst. After uptake of hydrogen (2 eq.), the catalyst was filtered off. The filtrate was evaporated and the residue was purified by column chromatography over silica gel (eluent: $CH_2Cl_2/CH_3OH$ 95/5). The pure fractions were collected and the solvent was evaporated, yielding 10 g (71%) of (±)-6,7,8,9-tetrahydro-3-(2-hydroxyethyl)-9-methoxy-2-methyl-4H-pyrido[1,2-a]-pyrimidin-4-one (intermediate 11).

EXAMPLE 6

Methanesulfonyl chloride (3.43 g) was added dropwise to a stirred and cooled (ice water bath) mixture of intermediate 13 (7 g) and N,N-diethylethanamine (3 g) in dichloromethane (50 ml). The reaction mixture was stirred for 2 hours at RT. The reaction mixture was washed with water and the organic layer was separated, dried over $MgSO_4$, filtered and the solvent was evaporated, yielding 8 g (84%) of (±)-6,7,8,9-tetrahydro-9-methoxy-2-methyl-3-[2-[(methylsulfonyl)oxy]ethyl]-4H-pyrido[1,2-a]pyrimidin-4-one (intermediate 12).

In a similar way, 2-(ethylthio)-3,6-dimethyl-5-[2-(methylsulfonyl)oxy]ethyl]-4(3H)-pyrimidinone hemihydradate (intermediate 13) was prepared from intermediate 3 and 2,3,6-trimethyl-5-[2-(methylsulfonyl)oxy]ethyl]-4(3H)-pyrimidinone (intermediate 14) was prepared from intermediate 5.

EXAMPLE 7 a) A mixture of intermediate 9 (170 g) and hydrobromic acid (48%) (1000 ml) was stirred and refluxed overnight. The mixture was cooled and the precipitate was filtered off, yielding a first fraction of 100 g. The filtrate was evaporated, yielding a second fraction of 30 g. Both fractions were recrystallized from water, yielding 75 g (34%) of 3-(2-bromoethyl)-9-hydroxy-2-methyl-4H-pyrido[1,2-a]pyrimidin-4-one monohydro-bromide (intermediate 15).

b) A mixture of intermediate 15 (55 g) and hydrobromic acid (48%) (55 g) in methanol (700 ml) was hydrogenated with palladium on activated carbon (10%) (5 g) as a catalyst. After completion, the precipitate was filtered off and the filtrate evaporated. Ammonium hydroxide was added to the residue which was subsequently extracted with $CHCl_3$. The separated organic layer was dried and evaporated. The residue was purified by column chromatography over silica gel (eluent: $CHCl_3/CH_3OH$ 90/10). The pure fractions were collected, the solvent was evaporated and the residue was recrystallized from 4-methyl-2-pentanone, yielding 17 g (44%) of (±)-6,7,8,9-tetrahydro-3-(2-bromoethyl)-9-hydroxy-2-methyl-4H-pyrido[1,2-a]pyrimidin-4-one (intermediate 16).

B. Preparation of the compounds of formula (I)

EXAMPLE 8

A mixture of 1-(4-piperidinyl)-1H-indole (4.1 g), 6-(2-chloroethyl)-7-methyl-5H-thiazolo[3,2-a]pyrimidin-5-one (3.4 g), prepared as described in EP-A-0,196,132, sodium carbonate (6 g) and potassium iodide (0.1 g) in 4-methyl-2-pentanone (250 ml) was stirred and refluxed overnight. The warm reaction mixture was filtered and the filtrate was evaporated. The residue was purified over silica gel on a glass filter (eluent: $CH_2Cl_2/C_2H_5OH$ 90/10). The pure fractions were collected and the solvent was evaporated. The residue was crystallized from DIPE with a small amount of CH3CN. The precipitate was filtered off and dried, yielding 3 g (51%) 6-[2-[4-(1H-indol-1-yl)-1-piperidinyl]ethyl]-7-methyl-5H-thiazolo[3,2-a]pyrimidin-5-one (compound 3; mp. 134.4° C.).

EXAMPLE 9

6-[2-[4-(1H-indol-1-yl)-1-piperidinyl]ethyl]-3,7-dimethyl-5H-thiazolo[3,2-a]pyrimidin-5-one was prepared according to the procedure described in example 7 without the presence of potassium iodide (compound 6; mp. 189.8° C.).

EXAMPLE 10

A mixture of 6-(2-chloroethyl)-2,7-dimethyl-5H-1,3,4-thiadiazolo[3,2-a]pyrimidin-5-one (3.6 g), prepared as described in EP-A-0,353,821, 5-fluoro-1-(4-piperidinyl)-1H-indole (3.3 g), prepared according to the procedure described in Synthetic Communications, 18 (3), 265-273 (1988), sodium carbonate (1 g), potassium iodide (catalytic quantity) and sodium hydrogen carbonate (2 g) in 4-methyl-2-pentanone (150 ml) and 2-ethoxyethanol (50 ml) was stirred and refluxed overnight. The mixture was filtered and the filtrate was washed with water. The organic layer was separated, dried, filtered and the solvent evaporated. The residue was purified by column chromatography over silica gel (eluent: $CH_2Cl_2/CH_3OH$ 95/5). The pure fractions were collected and the solvent was evaporated. The residue was crystallized from DIPE/CH3CN. The precipitate was filtered off, dried and purified by high-performance liquid chromatography over RP-18 (eluent: (0.5% $NH_4OAc$ in $H_2O$)/$CH_3OH$/THF 50/40/10). The pure fractions were collected and the solvent was evaporated, yielding 1.37 g (20%) 6-[2-[4-(5-fluoro-1H-indol-1-yl)-1-piperidinyl]-ethyl]-2,7-dimethyl-5H-1,3,4-thiadiazolo[3,2-a]pyrimidin-5-one (compound 8; mp. 194.1° C.).

EXAMPLE 11

A mixture of 6-(2-bromoethyl)-1,2,7-trimethyl-1H,5H-imidazo[1,2-a]pyrimidin-5-one (8.85 g), prepared as described in EP-0,378,255, 1-(4-piperidinyl)-1H-indole (2 g) and N-(1-methylethyl)-2-propanamine (1.2 g) in ethanol (100 ml) was stirred and refluxed for 6 hours. The solvent was evaporated and the residue was stirred in water and subsequently extracted with $CH_2Cl_2$. The separated organic layer was dried, filtered and the solvent was evaporated. The residue was purified by column chromatography over silica gel (eluent: $CH_2Cl_2/CH_3OH$ 95/5). The pure fractions were collected and the solvent was evaporated. The residue was crystallized from $CH_3CN$/DIPE and the precipitate was filtered off and dried, yielding 2.5 g (62%) 6-[2-[4-(1H-indol-1-yl)-1-piperidinyl]ethyl]-1,2,7-trimethylimidazo[1,2-a]pyrimidin-5(1H)-one (compound 9; mp. 165.7° C.).

EXAMPLE 12

1-(2-bromoethyl)-2H-benzimidazol-2-one (4.8 g) was added to a mixture of 1-(4-piperidinyl)-1H-indole (5.6 g), sodium methylate (1 g) and sodium carbonate (5 g) in 4-methyl-2-pentanone (250 ml). The reaction mixture was stirred and refluxed overnight. The mixture was filtered while still warm. The filtrate was evaporated. The residue was purified over silica gel on a glass filter (eluent: $CH_2Cl_2$/$C_2H_5OH$ 90/10). The pure fractions were collected and the solvent was evaporated. The residue was dissolved in warm ethanol and converted into the (E)-2-butenedioic acid salt (1:1). The mixture was cooled. The precipitate was filtered off and dried, yielding: 8.7 g (91%) 1,3-dihydro-1-[2-[4-(1H-indol-1-yl)-1-piperidinyl]ethyl]-2H-benzimidazol-2-one (E)-2-butenedioate (1:1) (compound 26; mp. 205.3° C.)

EXAMPLE 13

A mixture of 5-fluoro-1-(4-piperidinyl)-1H-indole (3.2 g), 1-(3-chloropropyl)-1,3-dihydro-2H-benzimidazol-2-one (3 g), N,N-diethylethanamine (3 ml) and potassium iodide (0.1 g) in toluene (200 ml) was stirred and refluxed overnight. The reaction mixture was cooled, washed with water and the organic layer was separated, dried, filtered and the solvent was evaporated. The residue was purified by column chromatography over silica gel (eluent: $CH_2Cl_2/CH_3OH$ 95/5). The pure fractions were collected and the solvent was evaporated. The residue was dissolved in ethanol and converted into the (E)-2-butenedioic acid salt (1:1). The mixture was allowed to cool, while stirring. The precipitate was filtered off and dried, yielding 3 g (42%) 1-[3-[4-(5-fluoro-1H-indol-1-yl)-1-piperidinyl]propyl]-1,3-dihydro-2H-benzimidazol-2-one (E)-2-butenedioate (1:1) (compound 28; mp. 192.5° C.).

Tables 1 to 4 list similar compounds that were prepared according to one of the above described examples.

TABLE 1

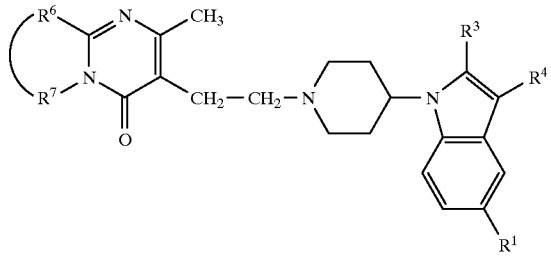

| Co. No. | Ex. No. | $R^1$ | $R^3$ | $R^4$ | —$R^6$—$R^7$— | Phys. Data (mp in ° C.) |
|---|---|---|---|---|---|---|
| 1 | 9 | H | H | H | —S—$CH_2$—$CH_2$— | 190.2 |
| 2 | 9 | F | H | H | —S—$CH_2$—$CH_2$— | 200.0 |
| 3 | 8 | H | H | H | —S—CH=CH— | 134.4 |
| 4 | 8 | F | H | H | —S—CH=CH— | 126.6 |
| 6 | 9 | H | H | H | —S—CH=C($CH_3$)— | 189.8 |
| 8 | 10 | F | H | H | —S—C($CH_3$)=N— | 194.1 |
| 9 | 11 | H | H | H | —N($CH_3$)—C($CH_3$)=CH— | 165.7 |
| 10 | 8 | F | H | H | —CH=C($CH_3$)—O— | 208.4 |
| 11 | 8 | H | H | H | —($CH_2$)$_4$— | 142.3 |

TABLE 1-continued

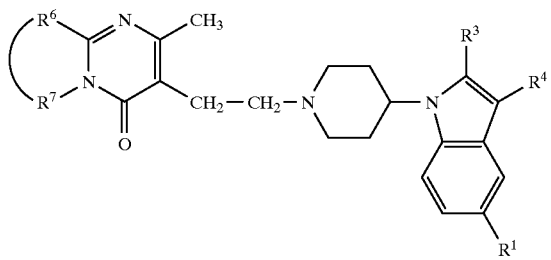

| Co. No. | Ex. No. | R¹ | R³ | R⁴ | —R⁶—R⁷— | Phys. Data (mp in °C.) |
|---|---|---|---|---|---|---|
| 12 | 8 | F | H | H | —(CH$_2$)$_4$— | 173.8 |
| 13 | 11 | H | H | H | —CH(OH)—(CH$_2$)$_3$— | (±)/154.4 |
| 14 | 11 | F | H | H | —CH(OH)—(CH$_2$)$_3$— | (±)/192.0 |
| 15 | 11 | F | H | H | —CH(OCH$_3$)—(CH$_2$)$_3$— | (±)/159.6 |
| 16 | 9 | H | H | H | —S—(CH$_2$)$_3$— | 153.0 |
| 17 | 9 | F | H | H | —S—(CH$_2$)$_3$— | 173.1 |
| 18 | 13 | F | H | H | —CH=CH—CH=CH— | 144.4 |
| 19 | 8 | H | H | H | —C(CH$_3$)=CH—CH=CH— | 127.6 |
| 20 | 8 | F | H | H | —C(CH$_3$)=CH—CH=CH— | 165.9 |
| 29 | 11 | F | H | H | —(CH$_2$)$_3$—CH(CH$_3$)— | 165.9 |
| 30 | 11 | F | —CH$_3$ | —C$_6$H$_5$ | —(CH$_2$)$_4$— | 147.7 |
| 32 | 11 | H | —CH$_3$ | H | —(CH$_2$)$_4$— | 140.2 |
| 33 | 11 | —OCH$_3$ | H | H | —(CH$_2$)$_4$— | 154.7 |
| 36 | 11 | H | —CH$_3$ | —CH$_3$ | —(CH$_2$)$_4$— | 149.2 |
| 37 | 11 | —CH$_3$ | H | H | —(CH$_2$)$_4$— | 161.2 |
| 38 | 11 | Cl | H | H | —(CH$_2$)$_4$— | 184.0 |

TABLE 2

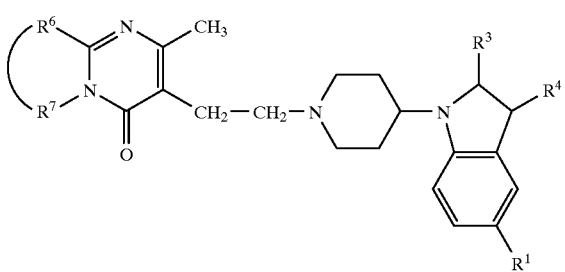

| Co. No. | Ex. No. | R¹ | R³ | R⁴ | —R⁶—R⁷— | Phys. Data (mp in °C.) |
|---|---|---|---|---|---|---|
| 5 | 11 | H | H | H | —S—CH=CH— | 143.4 |
| 31 | 11 | H | H | H | —(CH$_2$)$_4$— | 119.2 |
| 34 | 11 | H | —CH$_3$ | H | —(CH$_2$)$_4$— | 99.4 |
| 35 | 11 | H | —CH$_3$ | —CH$_3$ | —(CH$_2$)$_4$— | 123.7 |

TABLE 3

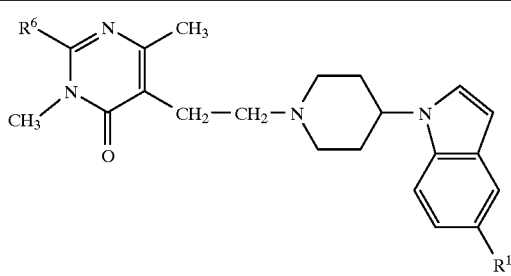

| Co. No. | Ex. No. | R¹ | R⁶ | Physic. Data (mp in °C.) |
|---|---|---|---|---|
| 21 | 11 | H | —CH$_3$ | 119.5 |
| 22 | 11 | H | —NH$_2$ | 210.7 |
| 23 | 8 | H | —NH—CH$_3$ | 171.9 |
| 24 | 8 | F | —NH—CH$_3$ | 179.8 |
| 25 | 11 | H | —S—CH$_2$—CH$_3$ | 129.5 |

TABLE 4

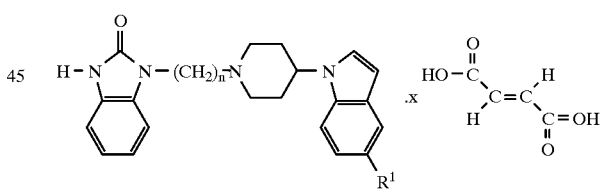

| Co. No. | Ex. No. | R¹ | n | x | Phys. Data (mp in °C.) |
|---|---|---|---|---|---|
| 26 | 12 | H | 2 | 1 | 205.3 |
| 27 | 9 | F | 2 | ½ | 179.8 |
| 28 | 13 | F | 3 | 1 | 192.5 |

C. Pharmacological Example

EXAMPLE 14

"apomorphine, tryptamine, norepinephrine (ATN) test in rats"

The antipsychotic activity of the subject compounds is evidenced by the experimental data obtained in the combined apomorphine (APO), tryptamine (TRY) and norepinephrine (NOR) test in rats. Said combined apomorphine, tryptamine and norepinephrine test is described in Arch. Int. Pharmacodyn., 227, 238–253 (1977) and provides an empirical evaluation of the relative specificity with which drugs may effect particular neurotransmitter systems centrally (CNS) as well as peripherally. In particular, the test demonstrates the antagonistic activity of the tested compounds of formula (I) on dopamine (by preventing the symptoms elicited with the dopamine agonist apomorphine), on serotonin (by preventing the central symptoms (convulsions) and peripheral symptoms (hyperaemia) elicited with serotonin or tryptamine), and on norepinephrine (by preventing or delaying death upon administration of the α-agonist norepinephrine). The favourable pharmacological property of the compounds of formula (I) lies in the absence of a strong α-adrenergic antagonistic activity (column NOR) laeding to an improved dissociation between peripheral α-adrenergic antagonistic activity and central serotonin (column TRY convulsions) and central dopamine (column APO) antagonistic activity.

The test is carried out following the procedures described in EP-A-0,196,132 and the experimental data are summarized in Table 5.

TABLE 5

| Compound Number | Combined test in rats, $ED_{50}$ in mg/kg | | | |
|---|---|---|---|---|
| | APO | TRY convulsions | TRY hyperaemia | NOR |
| 1 | 0.63 | 0.63 | 0.04 | >10 |
| 2 | 0.16 | 0.63 | 0.01 | 10 |
| 3 | 0.16 | 0.16 | 0.01 | >10 |
| 4 | 0.04 | 0.04 | 0.01 | 2.5 |
| 5 | 0.08 | 0.31 | 0.02 | >10 |
| 6 | 0.16 | 0.16 | 0.01 | 10 |
| 7 | 0.63 | 2.5 | 0.04 | >10 |
| 8 | 0.63 | 0.63 | 0.04 | 10 |
| 10 | 0.63 | 0.16 | 0.0025 | 10 |
| 12 | 0.31 | 0.31 | 0.02 | >10 |
| 15 | 0.16 | 0.63 | 0.01 | 10 |
| 16 | 0.16 | 0.63 | 0.02 | 10 |
| 17 | 0.08 | 0.16 | 0.02 | 5 |
| 18 | 0.08 | 0.08 | 0.01 | 5 |
| 19 | 0.63 | 2.5 | 0.63 | >10 |
| 20 | 0.63 | 0.63 | 0.16 | >10 |
| 24 | 0.63 | 0.16 | 0.01 | 10 |
| 25 | 0.63 | 2.5 | 0.16 | >10 |
| 28 | 0.16 | 0.16 | 0.01 | >10 |
| 29 | 0.08 | 0.31 | 0.005 | 5 |
| 31 | 1.25 | 1.25 | 0.31 | >10 |
| 34 | 5 | >10 | ≦0.63 | ≧10 |

D. Composition examples

"Active ingredient" (A.I.) as used throughout these examples relates to a compound of formula (I), a pharmaceutically acceptable addition salt or a stereochemically isomeric form thereof.

EXAMPLE 15

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE 16

Film-coated tablets
Preparation of tablet core
A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.
Coating
To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension and the whole is homogenated. The tablet cores are coated with the thus obtained mixture in a coating apparatus.

EXAMPLE 17

Oral solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 18

Injectable solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

We claim:
1. A compound of formula

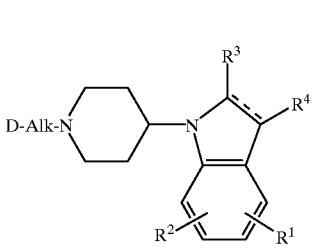

(I)

a pharmaceutically acceptable addition salt or a stereochemically isomeric form thereof, wherein:
the dashed line designates an optional bond;

R¹ and R² are each independently hydrogen, halogen, $C_{1-6}$alkyl or $C_{1-6}$alkyloxy;

R³ and R⁴ are each independently hydrogen, $C_{1-6}$alkyl, phenyl or phenyl substituted with one, two or three substituents selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl;

Alk is $C_{1-4}$alkanediyl;

D is a radical of formula

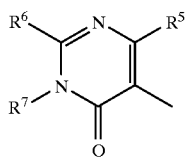
(a)

wherein

R⁵ is hydrogen or $C_{1-6}$alkyl;

R⁶ is hydrogen, $C_{1-6}$alkyl, $C_{1-6}$alkyloxy, $C_{1-6}$alkylthio, amino or mono- or di($C_{1-6}$alkyl)amino; and R⁷ is hydrogen or $C_{1-6}$alkyl; or R⁶ and R⁷ taken together may form a bivalent radical —R⁶—R⁷—, in particular, —R⁶—R⁷— may be —CH₂—CH₂—CH₂—; (a-1)

—CH₂—CH₂—CH₂—CH₂—; (a-2)

—CH=CH—CH₂—; (a-3)

—CH₂—CH=CH— or (a-4)

—CH=CH—CH=CH—; (a-5)

wherein one or two hydrogen atoms of said radicals (a-1) to (a-5) each independently may be replaced by $C_{1-6}$alkyl, hydroxy, $C_{1-6}$alkyloxy or $C_{1-6}$alkylcarbonyloxy; or
—R⁶—R⁷— may also be —S—CH₂—CH₂—; (a-6)

—S—CH₂—CH₂—CH₂—; (a-7)

—S—CH=CH—; (a-8)

—NH—CH₂—CH₂—; (a-9)

—NH—CH₂—CH₂—CH₂—; (a-10)

—NH—CH=CH—; (a-11)

—NH—CH=N—; (a-12)

—S—CH=N— or (a-13)

—CH=CH—O—; (a-14)

wherein one or where possible two or three hydrogen atoms in said radicals (a-6) to (a-14) each independently may be replaced by $C_{1-6}$alkyl;

or D is a radical of formula

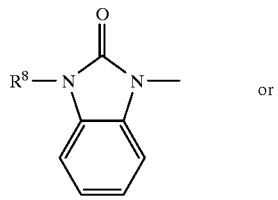
(b)

or

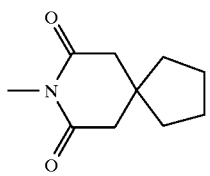
(c)

wherein R⁸ is hydrogen or $C_{1-6}$alkyl.

2. A compound according to claim 1, wherein D is a radical of formula

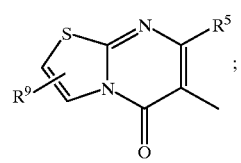
(d-1)

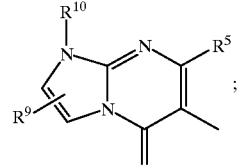
(d-2)

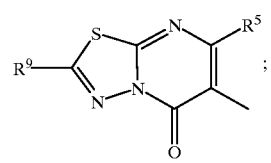
(d-3)

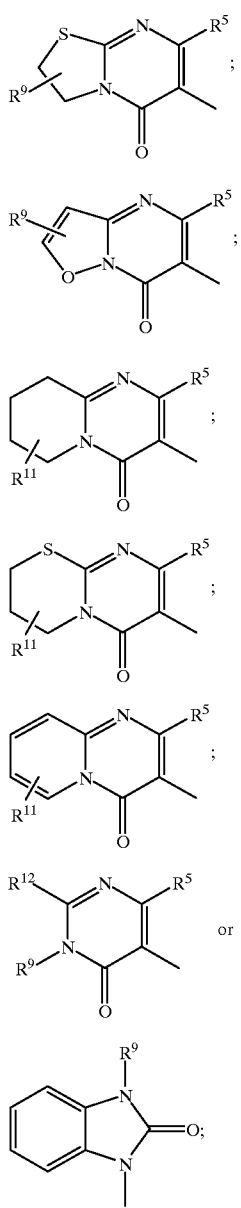

wherein $R^5$ is defined as in claim 1; $R^9$ and $R^{10}$ each independently are hydrogen or $C_{1-6}$alkyl; $R^{11}$ is $C_{1-6}$alkyl, hydroxy, $C_{1-6}$alkyloxy or $C_{1-10}$alkylcarbonyloxy; and $R^{12}$ is hydrogen, $C_{1-6}$alkyl, $C_{1-6}$alkyloxy, $C_{1-6}$alkylthio, amino or mono- or di($C_{1-6}$alkyl)amino.

3. A compound according to claim 1, wherein Alk is $C_{2-4}$alkanediyl.

4. A compound according to claim 1, wherein $R^1$ is hydrogen or halogen and $R^2$ is hydrogen.

5. A compound according to claim 1, wherein the compound is selected from

3-[2-[4-(5-fluoro-1H-indol-1-yl)-1-piperidinyl]ethyl]-6,7,8,9-tetrahydro-2-methyl-4H-pyrido[1,2-a]pyrimidin-4-one;

6-[2-[4-(5-fluoro-1H-indol-1-yl)-1-piperidinyl]ethyl]-7-methyl-5H-thiazolo-[3,2-a]-pyrimidin-5-one;

5-[2-[4-(5-fluoro-1H-indol-1-yl)-1-piperidinyl]ethyl]-3,6-dimethyl-2-(methylamino)-4(3H)-pyrimidinone; and 2,3-dihydro-6-[2-[4-(1H-indol-1-yl)-1-piperidinyl]ethyl]-7-methyl-5H-thiazolo-[3,2-a]pyrimidin-5-one; a pharmaceutically acceptable addition salt or a stereochemically isomeric form thereof.

6. A composition comprising a pharmaceutically acceptable carrier and, as active ingredient, a therapeutically effective amount of a compound as claimed in claim 1.

7. A composition comprising a pharmaceutically acceptable carrier and, as active ingredient, a therapeutically effective amount of a compound as claimed in claim 2.

8. A composition comprising a pharmaceutically acceptable carrier and, as active ingredient, a therapeutically effective amount of a compound as claimed in claim 3.

9. A composition comprising a pharmaceutically acceptable carrier and, as active ingredient, a therapeutically effective amount of a compound as claimed in claim 4.

10. A composition comprising a pharmaceutically acceptable carrier and, as active ingredient, a therapeutically effective amount of a compound as claimed in claim 5.

11. A method of treating psychotic diseases in patients in need of the same which comprises administering to said patients a therapeutically effective amount of a compound as claimed in claim 1.

12. A method of treating psychotic diseases in patients in need of the same which comprises administering to said patients a therapeutically effective amount of a compound as claimed in claim 2.

13. A method of treating psychotic diseases in patients in need of the same which comprises administering to said patients a therapeutically effective amount of a compound as claimed in claim 3.

14. A method of treating psychotic diseases in patients in need of the same which comprises administering to said patients a therapeutically effective amount of a compound as claimed in claim 4.

15. A method of treating psychotic diseases in patients in need of the same which comprises administering to said patients a therapeutically effective amount of a compound as claimed in claim 5.

* * * * *

UNITED STATES PATENT AND TRADEMARK OFFICE
CERTIFICATE OF CORRECTION

PATENT NO.   : 5,919,788
DATED        : July 6, 1999
INVENTOR(S)  : Jan Vandenberk, Ludo Edmond, Josephine Kennis, and Josephus Corolus It is certified that error appears in the above-identified patent and that said Letters Patent is hereby corrected as shown below:

Column 19, Claim 1:
Line 50: "or $C_{1-6}$alkylcarbonyloxy, or" should read: -- or $C_{1-10}$alkylcarbonyloxy; or --.

Signed and Sealed this

Twenty-eighth Day of August, 2001

*Attest:*

NICHOLAS P. GODICI
*Attesting Officer*   *Acting Director of the United States Patent and Trademark Office*